(12) United States Patent
Goddard

(10) Patent No.: US 10,736,724 B2
(45) Date of Patent: Aug. 11, 2020

(54) INSERTION DEVICES WITH VISUAL INDICATORS AND METHODS OF USING THE SAME

(71) Applicant: Boston Scientific Scimed, Inc., Maple Grove, MN (US)

(72) Inventor: James M. Goddard, Pepperell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 305 days.

(21) Appl. No.: 14/850,499

(22) Filed: Sep. 10, 2015

(65) Prior Publication Data

US 2016/0074146 A1  Mar. 17, 2016

Related U.S. Application Data

(60) Provisional application No. 62/049,598, filed on Sep. 12, 2014.

(51) Int. Cl.
| | | |
|---|---|---|
| A61B 17/00 | (2006.01) | |
| A61F 2/00 | (2006.01) | |
| A61B 17/34 | (2006.01) | |

(52) U.S. Cl.
CPC ........ *A61F 2/0045* (2013.01); *A61B 17/3468* (2013.01); *A61B 2017/00455* (2013.01); *A61B 2017/00805* (2013.01)

(58) Field of Classification Search
CPC .......... A61F 2/0063; A61F 2/0095; A61F 2002/0072; A61F 2/0045; A61B 17/3468; A61B 2017/00455; A61B 2017/00805
See application file for complete search history.

(56) References Cited

U.S. PATENT DOCUMENTS

| | | | | |
|---|---|---|---|---|
| 3,920,022 | A * | 11/1975 | Pastor ................ | A61B 18/1402 606/41 |
| 5,196,019 | A * | 3/1993 | Davis ................. | A61B 17/3403 378/81 |
| 2005/0033315 | A1* | 2/2005 | Hankins ............... | A61B 90/11 606/129 |
| 2011/0060319 | A1* | 3/2011 | Stocks .................. | A61B 90/30 606/4 |
| 2011/0130689 | A1* | 6/2011 | Cohen ............... | A61B 18/1477 601/3 |
| 2017/0000520 | A1* | 1/2017 | Shepherd .......... | A61B 17/3403 |

* cited by examiner

*Primary Examiner* — George J Ulsh
(74) *Attorney, Agent, or Firm* — Brake Hughes Bellermann LLP

(57) ABSTRACT

An insertion device, includes an elongate member having a needle portion and a handle portion. The handle portion includes a visual indicator. The visual indicator is configured to indicate an orientation of the needle portion.

10 Claims, 6 Drawing Sheets

INSERTION DEVICES WITH VISUAL INDICATORS AND METHODS OF USING THE SAME

CROSS-REFERENCE TO RELATED APPLICATION

This application is a Nonprovisional of, and claims priority to, U.S. Patent Application No. 62/049,598, filed on Sep. 12, 2014, entitled "INSERTION DEVICES WITH VISUAL INDICATORS AND METHODS OF USING THE SAME", which is incorporated by reference herein in its entirety.

BACKGROUND

Field

The present invention generally relates to surgical devices and procedures, particularly devices and methods for the delivery of implants within a patient's body.

Description of the Related Art

Anatomical tissues such as pelvic tissues may be weakened or damaged with age, injury, or disease. This decrease in structural integrity of anatomical tissues may have significant medical consequences, which in turn might influence the biological functions of the tissues. There are various surgical procedures for treating such dysfunction of the tissues. Implants can be placed into a patient to provide support for the weakened or damaged tissue. The support provided by the implant may replicate the natural position and structure of the tissue, and thereby help in decreasing or eliminating impairment of biological functions resulting from tissue weakening or damage.

Surgical methods may use an insertion device to deliver the implant to a location inside the patient's body. Such an insertion device may assist in the delivery and placement of the implant.

In view of the above, there is a need for an insertion device and a surgical procedure that may help facilitate the correct placement of the implant within the body of the patient and may help prevent puncturing or injury of other portions of the body of the patient (such as a bladder of the patient).

SUMMARY

In some embodiments, an insertion device, includes an elongate member having a needle portion and a handle portion. The handle portion includes a visual indicator. The visual indicator is configured to indicate an orientation of the needle portion. In some embodiments, the orientation of the needle portion is a tilt or angle of the needle portion. In some embodiment, the needle portion includes a curved portion and a linear portion. In some embodiments, the needle portion includes a curved portion and linear portion, the curve portion and the linear portion being disposed within a single plane.

In some embodiments, the visual indicator includes a groove defined by the handle portion. In some embodiments, the visual indicator includes a groove defined by the handle portion, the groove having a first side wall, a second side wall, and a floor disposed between the first side wall and the second side wall. In some embodiments, the visual indicator includes a groove defined by the handle portion, the groove having a first side wall, a second side wall, and a floor disposed between the first side wall and the second side wall, the first side wall being disposed within a first plane, the floor being disposed within a second plane, the second plane being orthogonal to the first plane. In some embodiments, the visual indicator includes a groove defined by the handle portion, the groove having a first side wall, a second side wall, and a floor disposed between the first side wall and the second side wall, the first side wall being disposed within a first plane, the floor being disposed within a second plane, the second side wall being disposed within a third plane, the first plane being parallel to the third plane, the second plane being orthogonal to the first plane and to the second plane. In some embodiments, the handle portion includes a proximal end portion and a distal end portion, the needle portion extends from the distal end portion of the handle portion, the visual indicator includes a groove defined by the handle portion, the groove extends from the distal end portion of the handle portion to the proximal end portion of the handle portion. In some embodiments, the visual indicator includes a linear groove defined by the handle portion. In some embodiments, the visual indicator includes a groove defined by the handle portion, the groove having a first side wall, a second side wall, and a floor disposed between the first side wall and the second side wall, the floor having a first color, the handle portion having a second color different than the first color. In some embodiments, the visual indicator includes a container and a fluid disposed within the container.

In some embodiments, the visual indicator includes a container, a fluid disposed within the container, and a marking. In some embodiments, the needle portion is disposed in a plane, the visual indicator includes a container and a fluid disposed within the container, the container extends orthogonal to the plane. In some embodiments, the needle portion includes a curved portion and a linear portion, the needle portion being disposed within a plane, the visual indicator includes a container and a fluid disposed within the container, the container extends orthogonal to the plane.

While features are described in detail for various embodiments, features of one embodiment may be used in another embodiment or combined with features of another embodiment.

In some embodiments, a method includes inserting a device into a body of a patient, the device including an elongate member having a needle portion and a handle portion, the handle portion including a visual indicator, the visual indicator being configured to indicate an orientation of the needle portion; and observing the visual indicator. In some embodiments, the method further includes moving the device in response to the indication provided by the visual indicator. In some embodiments, the method further includes advancing the device in the body of the patient. In some embodiments, the visual indicator includes a groove defined by the handle portion of the device. In some embodiments, the visual indicator includes a container and a fluid disposed within the container.

BRIEF DESCRIPTION OF THE FIGURES

The invention and the following detailed description of certain embodiments thereof may be understood with reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

The terms proximal and distal described in relation to various medical devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like, who may perform the procedure or surgery through the patient's body orifice or incision as described in the present invention. The term proximal refers to an area that is closer to the operator. The term distal refers to an area that is farther from the operator. The patient, as referred to here, can be a human female, male or any other mammal.

Although the present invention focuses on devices, systems and methods for use primarily for treatment of urinary incontinence, the disclosed devices, systems and methods may be used to treat any type of pelvic floor disorder or in any other procedure to place an implant within a body of a patient. In addition, the devices and methods may be used for delivering diagnostic or treatment devices to other parts of a patient's body with minimal damage to surrounding tissue. The present invention discloses devices that allow the operator to have greater control over the trajectory or movement of a needle of an insertion device to, for example, avoid inadvertent damage to surrounding tissue and accurately place the needle within the body of the patient.

Figure 1:
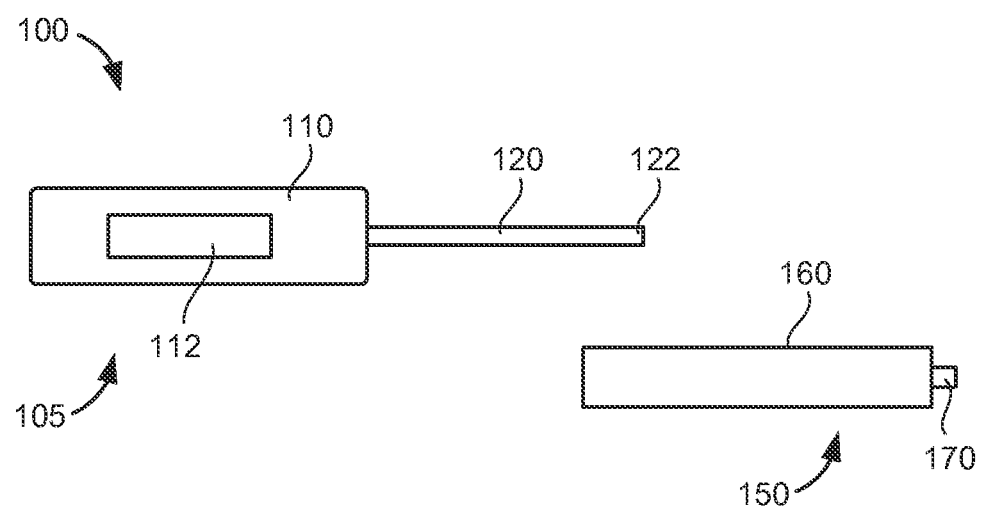
FIG. 1 is a schematic illustration of a medical system, according to an embodiment of the invention.
Figure 2:
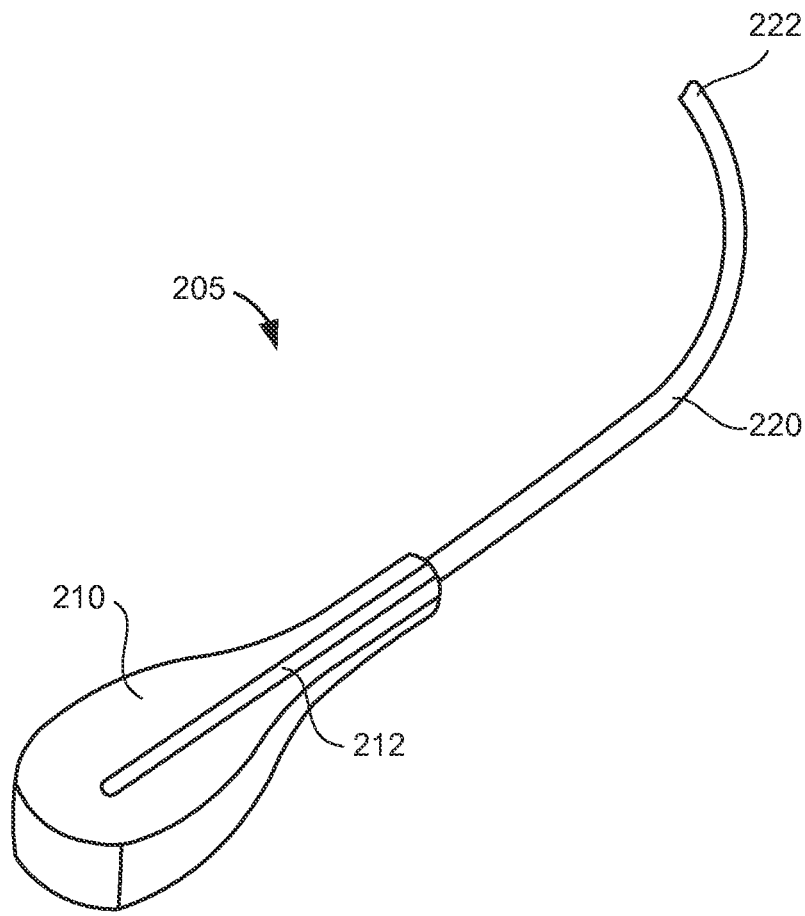
FIG. 2 is a perspective view of an insertion device, according to an embodiment of the invention.

FIG. 1 is a schematic illustration of a medical system 100 according to an embodiment of the invention. The medical system 100 includes an insertion device 105 and an implant 150. The insertion device 105 may be removably coupled to the implant 150 and may be configured to place or dispose the implant 150 within a body of a patient. For example, in some embodiments, the implant 150 is or includes a retropubic sling member and the insertion device 105 is configured to transvaginally place the implant 150 within the body of the patient. In other embodiments, the implant 150 is configured to be disposed in other portions of the body of the patient and the insertion device 105 is configured to deliver or place the implant 150 into such portion of the body of the patient.

In the illustrated embodiment, the insertion device 105 includes a handle portion 110 and needle portion 120. In some embodiments, the handle portion 110 is fixedly coupled to the needle portion 120. In some embodiments, the handle portion 110 is unitarily or monolithically formed with the needle portion 120. The needle portion 120 is configured to be inserted into a body of a patient and the handle portion 110 is configured to guide or be used to guide the needle portion 120 into and within the body of the patient. In some embodiments, the handle portion 110 is configured to be disposed outside of the body of the patient while the needle portion 120 is disposed within the body of the patient.

In the illustrated embodiment, the needle portion 120 includes a distal end portion 122. The distal end portion 122 may be configured to pierce and guide the needle portion 120 into and/or through bodily tissue. In some embodiments, the distal end portion 122 of the needle portion 120 is tapered or includes a sharp tissue piercing end.

In some embodiments, the needle portion 120 is non-linear or includes a curved portion. For example, in some embodiments, the needle portion 120 includes a single bend or curve. In some embodiments, the needle portion 120 is non-linear or curved and is disposed within a single plane.

In the illustrated embodiment, the handle portion 110 includes a visual indicator 112. The visual indicator 112 is configured to provide information about the orientation of the needle portion to the user, such as the physician. For example, in some embodiments, the visual indicator 112 is configured to indicate a direction in which the distal end portion 122 of the needle portion 120 is directed. In some embodiments, the visual indicator 112 is configured to indicate or identify when the insertion device 105 has been rotated or pivoted such that the needle portion 120 is pointed or directed in a direction away from a centerline or longitudinal axis of the insertion device 105. In some embodiments, the visual indicator 112 is configured to indicate or identify when the insertion device 105 has been rotated or pivoted such that the needle portion 120 is pointed or directed in a direction away from a plane that includes a centerline or longitudinal axis of the insertion device 105.

For example, in some embodiments, the insertion device 105 may be inserted into a body of a patient such that the needle portion 120 is disposed within the body of the patient and the handle portion 110 is disposed outside of the patient. The visual indicator 112 is configured to provide an indication or information to the user, such as the physician, about the orientation of the needle portion 120 which is disposed within the body of the patient. For example, in some embodiments, the visual indicator 112 may identify when the insertion device 105 has been pivoted or rotated such that the distal portion 122 of the needle portion 120 has been moved away from a centerline or center plane of the insertion device 105. Accordingly, the user, such as the physician, may appropriately direct, point, or advance the needle portion 120 of the insertion device 105 within the body of the patient.

In some embodiments, the insertion device 105 is configured to be removably coupled to the implant 150. In such embodiments, the insertion device 105 may be configured to advance or place the implant 150 into position within a body of a patient. In some embodiments, the needle portion 120 of the insertion device 105 may engage or communicate with a coupling portion 170 of the implant 150 to removably couple the implant 150 to the insertion device 105. The insertion device 105, while coupled to the implant 150, may then be inserted into the body of the patient. Once at the correct or desired location, the implant 150 may be removed from the insertion device 105 and the insertion device 105 may be removed from the body of the patient leaving the implant 150 in place within the body of the patient. In some embodiments, the insertion device 105 may then be coupled to another portion of the implant 150 and used to dispose or position that portion of the implant 150 within the body of the patient.

In the illustrated embodiment, the implant 150 includes a support portion 160. The support portion 160 is configured to provide support to a portion of the body of the patient. In some embodiments, the support portion 160 may be configured to be place within the body proximate the bodily portion that is to be supported. For example, in some embodiments, the implant 150 may be a sling, such as a sub-ureteral sling. The implant 150 may be formed of any biocompatible material. For example, in some embodiments, the implant 150 is a knitted material.

Figure 4:
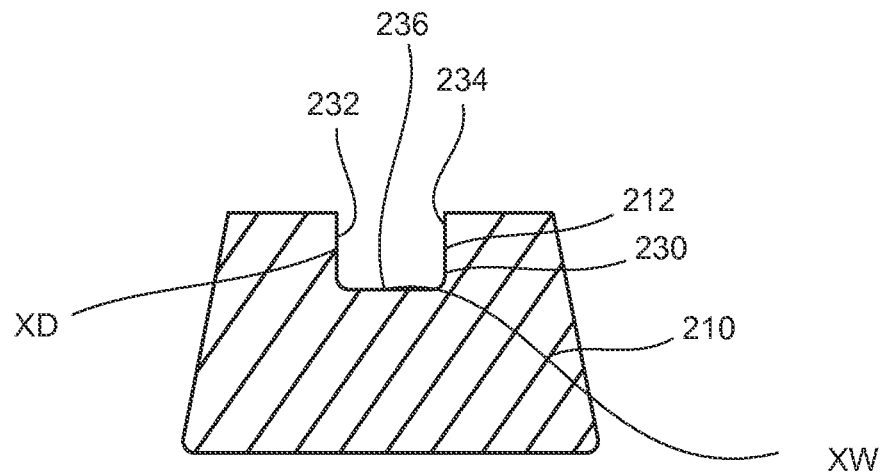
FIGS. 4 and 5 are cross-sectional views of the insertion device of FIG. 2 taken along line A-A of FIG. 3.
Figure 5:
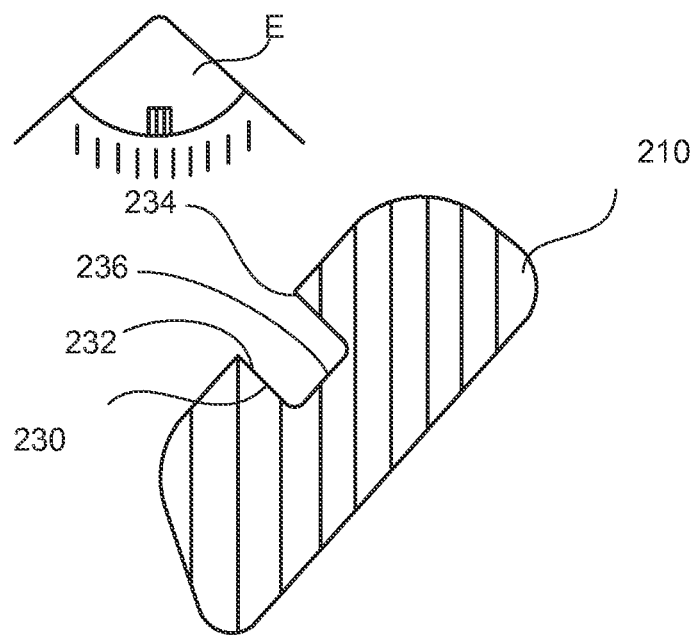
Figure 6:
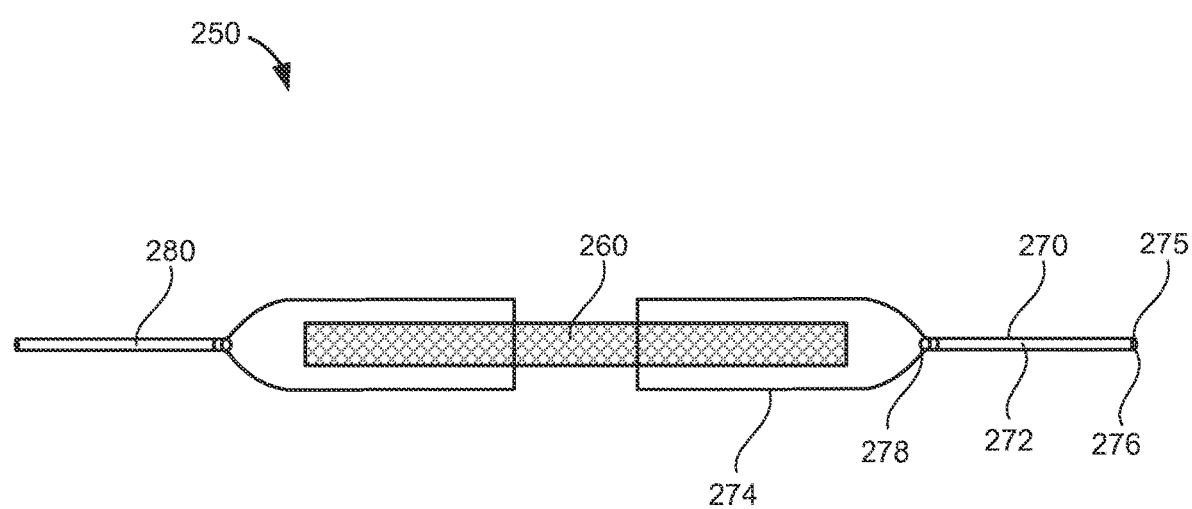
FIG. 6 is a top view of an implant according to an embodiment of the invention.

FIGS. 2 to 6 illustrate a medical system according to an embodiment of the invention. The medical system includes an insertion device 205 and an implant 250. FIGS. 2 to 5 illustrate the insertion device 205 and FIG. 6 illustrates the implant 250.

The insertion device 205 may be removably coupled to the implant 250 and may be configured to place or dispose the implant 250 within a body of a patient. For example, in the illustrated embodiment, the implant 250 is a retropubic sling member and the insertion device 205 is configured to transvaginally place the implant 250 within the body of the patient. In other embodiments, the implant 250 is configured to be disposed in other portions of the body of the patient and the insertion device 205 is configured to deliver or place the implant 250 into such portion of the body of the patient.

The insertion device 205 includes a handle portion 210 and needle portion 220. The needle portion 220 extends from the handle portion 210. In some embodiments, the handle portion 210 is fixedly coupled to the needle portion 220. In such embodiments, the needle portion 220 does not rotate with respect to the handle portion 210. In some embodiments, the handle portion 210 is unitarily or monolithically formed with the needle portion 220. The needle portion 220 is configured to be inserted into a body of a patient and the handle portion 210 is configured to guide or be used to help guide the needle portion 220 into and within the body of the patient. In some embodiments, the handle portion 210 is configured to be disposed outside of the body of the patient while the needle portion 220 is disposed within the body of the patient.

The needle portion 220 includes a distal end portion 222. The distal end portion 222 may be configured to pierce and guide the needle portion 220 into and/or through bodily tissue. In the illustrated embodiment, the distal end portion 222 of the needle portion 220 is tapered or includes a sharp tissue piercing end.

Figure 3:
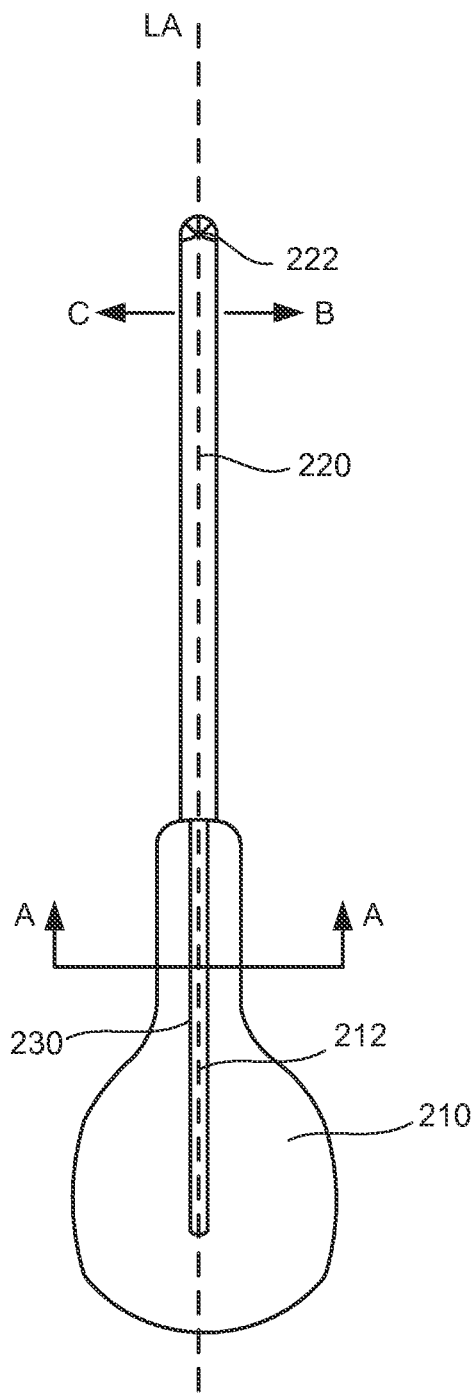
FIG. 3 is a top view of the insertion device of FIG. 2.

In the illustrated embodiment, the needle portion 220 is non-linear or includes a curved portion. Specifically, the needle portion 220 includes a single bend or curved portion. In the illustrated embodiment, the needle portion 220 is disposed within a single plane (for example, the plane P that includes the longitudinal axis or center line LA of the insertion device 205 and extends out of the page as shown in FIG. 3).

In the illustrated embodiment, the handle portion 210 includes a visual indicator 212. The visual indicator 212 is configured to provide information about the orientation of the needle portion 220 to the user, such as the physician. For example, in some embodiments, the visual indicator 212 is configured to indicate a direction in which the distal end portion 222 of the needle portion 220 is directed. In some embodiments, the visual indicator 212 is configured to indicate or identify when the insertion device 205 has been rotated or pivoted such that the needle portion 220 is pointed or directed in a direction away from a centerline or longitudinal axis LA of the insertion device 205. For example, the visual indicator 212 is configured to indicate or identify when the insertion device 205 has been rotated or pivoted such that the distal end portion 222 of the needle portion 220 has moved in the direction of arrow C or arrow B as illustrated in FIG. 3. Accordingly, the visual indicator 212 is configured to indicate or identify when the insertion device 205 has been rotated or pivoted such that the needle portion 220 is pointed or directed in a direction away from the plane P that includes the centerline or longitudinal axis LA of the insertion device 205.

In the illustrated embodiment, the visual indicator 212 includes groove or slot 230 that is defined by or in the handle portion 210. As best illustrated in FIGS. 4 and 5, the groove or slot includes a first side wall 232, a second side wall 234, and a base or floor 236. The base or floor 236 is disposed between and extends from the first side wall 232 and the second side wall 234. In the illustrated embodiment, the first side wall 232 is disposed orthogonal to the base or floor 236 and is parallel to the second side wall 234. More specifically, the first side wall 232 is disposed in a plane that is orthogonal to a plane in which the base or floor 236 is disposed within. The plane that the first side wall 232 is disposed within is parallel to the plane that the second side wall is disposed within. In other embodiments, the side walls are not disposed orthogonally to the base or floor.

In some embodiments, the groove or slot 230 can have any dimensions. The larger or smaller the dimensions of the groove or slot 230 different amounts of the base or floor 236 will be visible as the insertion device 205 is pivoted or rotated, as described in more detail below. In some embodiments, the groove or slot 230 is about 15 mm deep (XD as shown in FIG. 4) and is about 15 mm wide (XW as shown in FIG. 4). In other embodiments, the groove or slot is greater than 15 mm deep. In yet other embodiments, the groove or slot 230 is less than 15 mm deep. In some embodiments, the groove is greater than 15 mm wide. In yet other embodiments, the groove or slot 230 is less than 15 mm wide. In some embodiments, the width of the slot is less than the depth of the slot. For example, in some embodiments, the width of the slot is between 2 and 6 mm and the depth of the slot is between 7 and 20 mm.

In the illustrated embodiment, the groove or slot 230 is linear and extends along the longitudinal axis LA of the insertion device 205. In some embodiments, the groove or slot 230 extends along the entire length of the handle portion 210. In other embodiments, the groove or slot 230 only extends along a portion of the handle portion 210. In some embodiments, the groove or slot is non-linear or includes a curved portion and a linear portion.

In the illustrated embodiment, the base or floor 236 (or the upper surface of the base or floor 237) is of a color that is different than the color of the handle portion 210. In some embodiments, the base or floor 236 is of a color that is different than the color of the portion of the handle portion 210 that is immediately adjacent the groove or slot 230. For example, in some embodiments, the handle portion 210 is blue and the base or floor 236 is red. In other embodiments, other colors are used.

In the illustrated embodiment, the different colors of the base or floor 236 and the handle portion 210 allow the user of the insertion device 205 to determine when the insertion device 205 has been pivoted or rotated. Accordingly, the user of the insertion device 205 may determine the position or orientation of the needle portion 220 while the needle portion 220 is disposed within the body of the patient.

For example, as illustrated, in FIG. 5, when the insertion device 205 is rotated or pivoted, the user (schematically illustrated by the eye E), the view of the base or floor will be blocked or obscured and in some cases if rotated or pivoted enough the user will not be able to see the base or floor 236. Thus, the user may determine the orientation or position of the needle portion 220 (including the distal end portion 222) within the body of the patient. For example, in some embodiments, if the insertion device 205 is rotated or pivoted more than 75 degrees from a vertical position of the needle portion 220, the user's view of the base or floor will be blocked. In other embodiments, if the insertion device 205 is rotated or pivoted more than 25 degrees from a vertical position of the needle portion 220, the user's view of the base or floor will be blocked. In yet other embodiments, if the insertion device is rotated or pivoted more than 10 degrees from a vertical position of the needle portion 220, the user's view of the base or floor will be blocked.

The insertion device 205 may be inserted into a body of a patient such that the needle portion 220 is disposed within the body of the patient and the handle portion 210 is disposed outside of the patient. The visual indicator 212 is configured to provide an indication or information to the user, such as the physician, about the orientation of the needle portion 220 which is disposed within the body of the patient. For example, in some embodiments, the visual indicator 212 may identify when the insertion device 205 has been pivoted or rotated such that the distal portion 222 of the needle portion 220 has been moved away from a centerline or center plane of the insertion device 205. Accordingly, the user, such as the physician, may appropriately direct, point, or advance the needle portion 220 of the insertion device 205 within the body of the patient.

The implant 250 can be any type of bodily implant or device configured to be placed within a body of a patient. In some embodiments, the implant 250 is configured to be placed within the body of a patient and provide support to a portion of the body of the patient. For example, in some embodiments, the implant 250 can be placed within the body of the patient and provide support to a urethra, bladder, or other pelvic organ. In other embodiments, implant 250 may provide support to another portion of the body or may provide a different function.

In the illustrated embodiment, the implant 250 includes a support portion 260, a first delivery system 270, and a second delivery system 280. The delivery systems 270 and 280 may be used help deliver or place the implant 250 (the support portion 260) within the body of the patient. In the illustrated embodiment, the first delivery system 270 is removably coupled to a first end portion of the support portion 260 and the second delivery system 280 is removably coupled to a second end portion of the support portion 260. The first and second delivery systems 270 and 280 are structurally and functionally similar. Accordingly, only the first delivery system 270 will be described in detail.

The first delivery system 270 includes a dilator 272 and a sleeve 274. The dilator 272 is configured to help dilate bodily tissue while the implant 250 is placed within the body of the patient. The dilator 272 defines a lumen 275 that is configured to receive the needle portion 220 or a portion of the needle portion 220 to removably couple the implant 250 to the delivery device 205. In the illustrated embodiment, the lumen 275 extends from opening 276 defined by the dilator 272 to opening 278 defined by the dilator 272. The dilator 272 is coupled to the sleeve 274. The dilator 272 may be coupled to the sleeve 274 via any known coupling mechanism. For example, a heat seal or an adhesive such as glue may be used to couple dilator 272 to the sleeve 274.

The sleeve 274 defines a cavity or opening and surrounds a portion of the support portion 260 of the implant 250. The sleeve 274 is configured to help protect the support portion 260 of the implant 250 when the implant 250 is inserted into the body of the patient. The sleeve 274 is removably coupled to the support portion 260. Any known coupling mechanism may be used to couple the sleeve 274 to the support portion 260. For example, a heat seal, glue, or other coupling mechanism may be used to couple the sleeve 274 to the support portion 260.

In other embodiments, the implant includes different delivery systems. For example, the implant may include delivery systems that include different mechanisms for removably coupling to the needle portion of the delivery member. In some embodiments, the implant includes a suture or filament that forms a loop that is configured to engage a slot or other portion of the needle portion to removably couple the implant to the needle portion.

Figure 7:
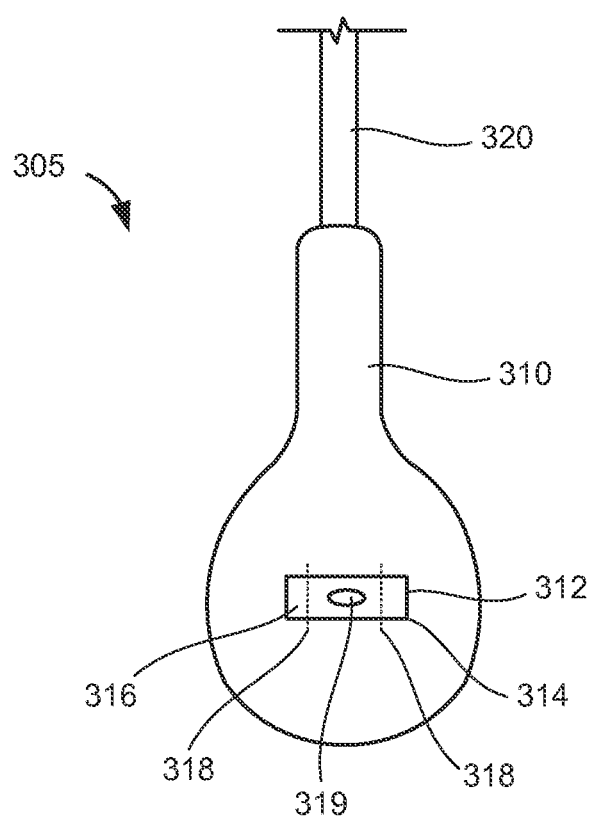
FIG. 7 is a top view of an insertion device according to an embodiment of the invention.

FIG. 7 is a top view of a portion of an insertion device 305 according to an embodiment of the invention. The insertion device 305 includes a handle portion 310 and a needle portion 320. The handle portion includes a visual indictor 312. The visual indicator 312 is configured to indicate to a user, such as a physician, the orientation or position of the needle portion 320. Specifically, the visual indicator 312 is configured to indicate when the insertion device 305 has been pivoted or rotated such that the needle portion 320 may extend or be directed away from a longitudinal axis of the insertion device 305.

In some embodiments, the needle portion 320 is non-linear and includes a curved portion. In some embodiments, the needle portion 320 is non-linear and is disposed within a plane.

The visual indicator 312 includes a container 314, a fluid 316 disposed within the container 314, and a set of markings 318. In the illustrated embodiment, the fluid 316 does not fill the entire container 314 and an air bubble 319 is also disposed within the container 314. As the insertion device 305 is rotated or pivoted the fluid 316 and the air bubble 319 will move within the container 314. Accordingly, the visual indicator 312 may indicate to the user when the insertion device 305 has been rotated or pivoted. The fluid 316 may be any type of fluid that will move within the container 314 when the insertion device 305 is rotated or pivoted. For example, the fluid may be a liquid such as water or oil.

The markings 318 may be used to help indicate to the user when the insertion device 305 has been pivoted or rotated. For example, in some embodiments, the air bubble 319 may be disposed within a pair of markings to indicate that that the insertion device 305 has not been pivoted or rotated. The air bubble 319 may be disposed on one side or the other side of the pair of markings to indicate that then insertion device 305 has been pivoted or rotated. In other embodiments, the markings 318 may indicated or help provide an indication to a user as to how much or to what extend the insertion device 305 has been pivoted or rotated. The air bubble 319 is an example of a gas that is less dense than the fluid. In other embodiments, the bubble may be of another gas or material that is less dense than the fluid. In some embodiments, the air bubble is disposed or encapsulated within a container.

In the illustrated embodiment, the container 314 is linear and extends along an axis CA. The axis CA is orthogonal or perpendicular to the longitudinal axis LA2 of the insertion device 305. In other embodiments, the container 314 has a different orientation with respect to the handle portion 310 or the insertion device 305.

Figure 8:
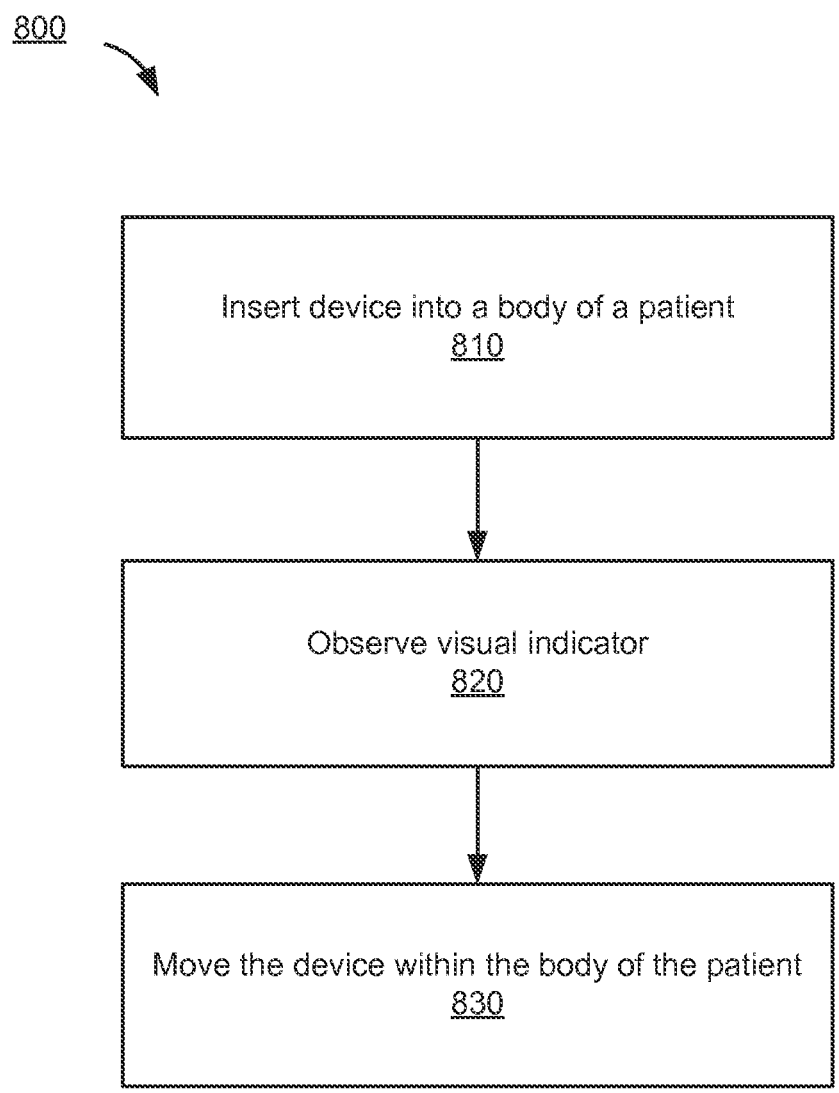
FIG. 8 is a flow chart illustrating a method according to an embodiment of the invention.

FIG. 8 is a flow chart that illustrated a method 800 according to an embodiment of the invention. In some embodiments, the insertion device (such as 205 or 305) may be coupled to a first end portion of an implant (such as 250). For example, in some embodiments, the insertion device may be removably coupled to a first end portion of the implant by inserting the needle portion of the insertion device into a lumen defined by a dilator of the implant.

At 810, the insertion device and the first end portion of the implant may be inserted into a body of a patient. For example, in some embodiments, the insertion device and the first end portion of the implant are inserted into a body of a patient via a vaginal incision. In other embodiments, the insertion device and implant may be inserted into another portion of the body of the patient.

At 820, as the insertion device and the first end portion of the implant are inserted into the body of the patient, the visual indicator may be observed to determine if the insertion device has been pivoted or rotated such that the needle portion has extended or is directed in a direction too far laterally or off of the centerline or longitudinal axis of the insertion device. For example, in some embodiments, when inserting a retropubic sling via a vaginal incision, the physician may track the needle against a posterior side of the pubic symphysis to ensure that the needle does not travel too far cephalad. Additionally, the physician may also use the visual indicator to identify or determine when (or if) the needle has traveled too far laterally.

At 830, the insertion device may be used to advance the implant within the body of the patient. Once at a desired location, the implant may be removed or decoupled from the insertion device and the insertion device may be removed from the body leaving the implant (such as the first end portion of the implant) within the body of the patient.

In some embodiments, the above procedure may be used to place the second end portion of the implant into the body of the patient (thereby disposing the entire implant within the body of the patient). In some embodiments, the implant includes more than two end portions or arms that can be inserted using the above procedure.

In some embodiments, the insertion device may be coupled to the implant by inserting the needle portion of the insertion device into a lumen defined by the dilator of the implant. The insertion device may be inserted into a body of the patient via a vaginal incision. The insertion device and implant may be advanced to extend through a skin incision such as a skin incision in the abdomen region of the patient. The physician may then grasp the dilator or portion of the dilator that extends through the skin incision and retract the needle portion from the lumen of the dilator to decouple the dilator from the insertion device.

In some embodiments, an insertion device, includes an elongate member having a needle portion and a handle portion. The handle portion includes a visual indicator. The visual indicator is configured to indicate an orientation of the needle portion. In some embodiments, the orientation of the needle portion is a tilt or angle of the needle portion. In some embodiment, the needle portion includes a curved portion and a linear portion. In some embodiments, the needle portion includes a curved portion and linear portion, the curve portion and the linear portion being disposed within a single plane.

In some embodiments, the visual indicator includes a groove defined by the handle portion. In some embodiments, the visual indicator includes a groove defined by the handle portion, the groove having a first side wall, a second side wall, and a floor disposed between the first side wall and the second side wall. In some embodiments, the visual indicator includes a groove defined by the handle portion, the groove having a first side wall, a second side wall, and a floor disposed between the first side wall and the second side wall, the first side wall being disposed within a first plane, the floor being disposed within a second plane, the second plane being orthogonal to the first plane. In some embodiments, the visual indicator includes a groove defined by the handle portion, the groove having a first side wall, a second side wall, and a floor disposed between the first side wall and the second side wall, the first side wall being disposed within a first plane, the floor being disposed within a second plane, the second side wall being disposed within a third plane, the first plane being parallel to the third plane, the second plane being orthogonal to the first plane and to the second plane. In some embodiments, the handle portion includes a proximal end portion and a distal end portion, the needle portion extends from the distal end portion of the handle portion, the visual indicator includes a groove defined by the handle portion, the groove extends from the distal end portion of the handle portion to the proximal end portion of the handle portion. In some embodiments, the visual indicator includes a linear groove defined by the handle portion. In some embodiments, the visual indicator includes a groove defined by the handle portion, the groove having a first side wall, a second side wall, and a floor disposed between the first side wall and the second side wall, the floor having a first color, the handle portion having a second color different than the first color. In some embodiments, the visual indicator includes a container and a fluid disposed within the container.

In some embodiments, the visual indicator includes a container, a fluid disposed within the container, and a marking. In some embodiments, the needle portion is disposed in a plane, the visual indicator includes a container and a fluid disposed within the container, the container extends orthogonal to the plane. In some embodiments, the needle portion includes a curved portion and a linear portion, the needle portion being disposed within a plane, the visual indicator includes a container and a fluid disposed within the container, the container extends orthogonal to the plane.

While features are described in detail for various embodiments, features of one embodiment may be used in another embodiment or combined with features of another embodiment.

In some embodiments, a method includes inserting a device into a body of a patient, the device including an elongate member having a needle portion and a handle portion, the handle portion including a visual indicator, the visual indicator being configured to indicate an orientation of the needle portion; and observing the visual indicator. In some embodiments, the method further includes moving the device in response to the indication provided by the visual indicator. In some embodiments, the method further includes advancing the device in the body of the patient. In some embodiments, the visual indicator includes a groove defined by the handle portion of the device. In some embodiments, the visual indicator includes a container and a fluid disposed within the container.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this invention. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the disclosure.

What is claimed is:

1. An insertion device, comprising:
   an elongate member having a needle portion and a handle, the elongate member having a proximal end and a distal end to define a longitudinal centerline,
   the handle including a visual indicator, the visual indicator being extended substantially along an entire length of the longitudinal centerline of the handle, the visual indicator being configured to indicate when the insertion device has been moved such that the needle portion is directed in a direction away from the longitudinal centerline, and
   the visual indicator includes a groove defined by the handle, the groove having a first side wall, a second side wall, and a floor disposed between the first side wall and the second side wall.

2. The insertion device of claim 1, wherein the needle portion includes a curved portion and a linear portion.

3. The insertion device of claim 1, wherein the needle portion includes a curved portion and linear portion, the curve portion and the linear portion being disposed within a single plane.

4. The insertion device of claim 1, wherein the first side wall is disposed within a first plane, the floor is disposed within a second plane, and the second plane is orthogonal to the first plane.

5. The insertion device of claim 1, wherein the first side wall is disposed within a first plane, the floor is disposed within a second plane, and the second side wall is disposed within a third plane,
   wherein the first plane is parallel to the third plane, and the second plane is orthogonal to the first plane and to the second plane.

6. The insertion device of claim 1, wherein the handle includes a proximal end portion and a distal end portion, the needle portion extends from the distal end portion of the handle, and the groove extends from near the distal end portion of the handle portion to the proximal end portion of the handle portion.

7. The insertion device of claim 1, wherein the visual indicator includes a linear groove defined by the handle portion.

8. The insertion device of claim 1, wherein the floor of the visual indicator has a first color, and the handle has a second color different than the first color.

9. An insertion device, comprising:
   an elongate member having a needle portion and a handle, the elongate member having a proximal end and a distal end to define a longitudinal centerline,
   the handle including a visual indicator, the visual indicator being configured to indicate when the insertion device has been moved such that the needle portion is directed in a direction away from the longitudinal centerline, and
   the visual indicator includes a groove defined by the handle, the groove having a first side wall, a second side wall, and a floor disposed between the first side wall and the second side wall,
   the floor of the visual indicator has a first color and a portion of the handle has a second color different than the first color.

10. The insertion device of claim 9, wherein the visual indicator is disposed at the proximal end of the handle portion.

* * * * *